United States Patent [19]

Kirchner

[11] Patent Number: 5,414,111
[45] Date of Patent: May 9, 1995

[54] POLYFLUORO NITROGEN-CONTAINING ORGANIC COMPOUNDS

[75] Inventor: Jack R. Kirchner, Wilmington, Del.

[73] Assignee: E. I. Du Pont de Nemours and Company, Wilmington, Del.

[21] Appl. No.: 190,704

[22] Filed: Feb. 2, 1994

Related U.S. Application Data

[63] Continuation of Ser. No. 34,628, Mar. 22, 1993, abandoned, which is a continuation of Ser. No. 790,097, Nov. 6, 1991, abandoned, which is a continuation-in-part of Ser. No. 459,060, Dec. 29, 1989, abandoned.

[51] Int. Cl.$^6$ .............. C07C 265/02; C07C 265/14; C07C 275/14; D06M 15/576
[52] U.S. Cl. .................... 560/357; 560/337; 560/358; 560/359; 564/38; 564/54; 252/8.6; 252/8.75; 252/8.8; 252/8.7; 428/224; 428/288; 428/289; 428/319.3; 544/221; 544/222

[58] Field of Search .............. 560/357, 359, 337, 358; 564/38, 54; 544/221, 222

[56] References Cited

U.S. PATENT DOCUMENTS 3,987,227 10/1976 Schultz et al. ............... 428/91
4,877,540 10/1989 Engelhardt et al. .......... 560/359

Primary Examiner—Floyd D. Higel

[57] ABSTRACT

Polyfluoro organic compound having at least one urea linkage derived from: (1) at least one polyisocyanate containing at least three isocyanate groups, (2) at least one fluorochemical compound which contains per molecule (a) a single functional group having one or more Zerewitinoff hydrogen atoms and (b) at least two carbon atoms each of which contains at least two fluorine atoms, and (3) water in an amount sufficient to to react with from about 5% to about 60% of the isocyanate groups.

24 Claims, No Drawings

POLYFLUORO NITROGEN-CONTAINING ORGANIC COMPOUNDS

This is a continuation of application Ser. No. 08/034,628 filed Mar. 22, 1993, now abandoned which is a continuation of application Ser. No. 07/790,097 filed Nov. 6, 1991, now abandoned which is a continuation-in-part of application Ser. No. 07/459,060 filed Dec. 29, 1989, now abandoned.

FIELD OF THE INVENTION

The present invention relates to novel water-modified fluorochemical nitrogen-containing compounds which are useful to provide oil-, water- and soil-repellency and/or soil-release properties, The foregoing uses of the compounds of this invention are disclosed and claimed in my copending application Ser. No. 07/459,040, and the manufacture of the compounds of this invention is disclosed and claimed in my copending application Ser. No. 07/459,035, both of which copending applications were filed of even date herewith.

BACKGROUND OF THE INVENTION

U.S. Pat. No. 3,987,227 discloses carpets having a stain-repellent and soil-resistant coating formed by a combination of a water-insoluble fluoroaliphatic radical containing urethane adduct and a water insoluble urethane adduct free from fluoroaliphatic radicals. The urethane adducts were prepared from polyisocyanates in accordance with the process disclosed in U.S. Pat. No. 3,484,281; as is conventional with reactions involving isocyanates, anhydrous conditions were maintained.

U.S. Pat. No. 4,264,484 discloses treating carpets with a combination of:
(a) a water-insoluble addition polymer derived from polymerizable ethylenically unsaturated monomer; and
(b) a water-insoluble fluoroaliphatic radical and aliphatic chlorine-containing carboxylic or carbamic ester.

U.S. Pat. No. 4,340,749 discloses treating carpets to render them soil-resistant and stain-repellent with a carboxylic or carbamic ester of a fluoro-aliphatic radical- and aliphatic chlorine-containing alcohol.

U.S. Pat. No. 4,401,780 discloses treating textiles with a fluorochemical composition comprising a mixture of:
(a) a water-insoluble fluoroaliphatic radical and aliphatic chlorine-containing ester;
(b) a water-insoluble fluoroaliphatic radical-containing polymer; and
(c) water insoluble fluoroaliphatic radical-containing compound selected from carbonylimino compounds and imine compounds.

U.S. Pat. No. 4,504,401 discloses polyfluoroalkyl compounds, said to be useful as stain proofing agents, which are obtained by reacting a polyfluoroalkyl-containing alcohol with a polyfunctional isocyanate compound containing at least three isocyanate groups. In addition to the polyfluoroalkyl-containing compounds, nonfluorinated compounds may be reacted with the polyisocyanate, most notably stearyl alcohol. Reaction of the polyisocyanate with the polyfluoroalkyl-containing compound and the nonfluorinated compounds are carried out sequentially. Substantially anhydrous conditions are used for those reactions, because the presence of water is indicated to be disadvantageous to the isocyanate group.

U.S. Pat. No. 4,668,406 discloses fluorochemical biurets which have one or more monovalent fluoroaliphatic radicals and one or more biuret moieties, and can contain organoamino or acid moieties. The fluorochemical biurets are said to be useful for the treatment of fibrous substrates to impart oil- and water-repellency. Various reaction schemes are disclosed, none of which discloses the use of water as a reactant; in the experiments described in the EXAMPLES, the reactions are conducted under nitrogen.

Br. 1,241,505 discloses tertiary amine salts of fluorocarbamates which are useful as oil-repellents for treating fabrics.

U.S. Pat. No. 3,201,372 discloses reacting a stoichiometric excess of a polyisocyanate with a polyol containing no fluorine, then reacting the resulting free isocyanate-containing prepolymer with water so as to produce a polymeric foam.

SUMMARY OF THE INVENTION

The present invention relates to novel fluorochemical nitrogen-containing compounds which when applied to fibers and fabrics provide durable water-, oil-, and soil-repellent and/or soil-release properties to the fibrous substrates. It relates also to substrates treated with the novel fluorochemical compounds of the invention. It relates further to processes for imparting water-, oil-, and soil-repellency and/or soil-release properties to fibrous substrates wherein the novel compounds of the invention are applied to the substrates. It relates in addition to novel processes for preparing the novel fluorochemical compounds of the invention.

DETAILED DESCRIPTION OF THE INVENTION

The polyfluoro organic compounds of the present invention comprise compounds having at least one urea linkage per molecule which compounds are derived from: (1) at least one polyisocyanate or mixture of polyisocyanates which contains at least three isocyanate groups per molecule, (2) at least one fluorochemical compound which contains per molecule (a) a single functional group having one or more Zerewitinoff hydrogen atoms[1] and (b) at least two carbon atoms each of which contains at least two fluorine atoms, and (3) water in an amount sufficient to react with from about 5% to about 60% of the —NCO groups in the polyisocyanate. In a preferred embodiment, the amount of water is sufficient to react with about 10% to about 35% of the isocyanate groups in the polyisocyanate, and most preferably, between about 15% and about 30%.

[1]Zerewitinoff et al. method: an active hydrogen-containing organic compound [—OH, —COOH, —NH, etc.] is reacted with a $CH_3Mg$ halide to liberate $CH_4$ which, measured volumetrically, gives a quantitative estimate of the active hydrogen content of the compound. Primary amines give 1 mol of $CH_4$ when reacted in the cold; usually 2 mols when heated [Organic Chemistry by Paul Karrer, English Translation published by Elsevier 1938, page 135].

A wide variety of fluorochemical compounds which contain a single functional group can be used so long as each fluorochemical compound contains at least two carbon atoms and each carbon atom contains at least two fluorine atoms. For example, the fluorochemical compound can be represented by the formula:

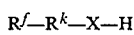

wherein $R^f$ is a monovalent aliphatic group containing at least two carbon atoms each of which contains at least two flourine atoms;

R is a divalent organic radical;

k is 0 or 1; and

X is —O—, —S—, or —N(R$^1$)—[2] in which R$^1$ is H, alkyl containing 1 to 6 carbon atoms or

[2] For purposes of this invention, it is assumed that a primary amine provides one active hydrogen as defined by Zerewitinoff et al. a $R^f$—$R_k$— group.

In a more specific embodiment, the fluorochemical compound which contains a single functional group can be represented by the formula:

$$R^f-R^k-R^2-X-H$$

wherein $R^f$ and k are as defined above;

R is the divalent radical: —C$_m$H$_{2m}$SO—, —C$_m$H$_{2m}$SO$_2$—, —SO$_2$N(R$^3$)—, or —CON(R$^3$)— in which m is 1 to 22 and R$^3$ is H or alkyl of 1 to 6 carbon atoms;

R$^2$ is the divalent linear hydrocarbon radical: —C$_n$H$_{2n}$— which can be optionally end-capped by

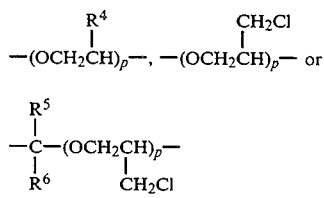

in which n is 0 to 12, p is 1 to 50, and R$^4$, R$^5$ and R$^6$ are the same or different H or alkyl containing 1 to 6 carbon atoms; and X is —O—, —S—, or —N(R$^7$)— in which R$^7$ is H, alkyl containing 1 to 6 carbon atoms or a $R^f$—$R_k$—R$^2$— group.

More particularly, $R^f$ is a fully-fluorinated straight or branched aliphatic radical of 3 to 20 carbon atoms which can be interrupted by oxygen atoms.

In a preferred embodiment, the fluorochemical compound which contains a single functional group can be represented by the formula:

$$R^f-(CH_2)_q-X-H$$

wherein

X is —O—, —S—, or —N(R$^7$)— in which R$^7$ is H, alkyl containing 1 to 6 carbon atoms or a $R^f$—$R_k$—R$^2$— group.

$R^f$ is a mixture of perfluoroalkyl groups, CF$_3$CF$_2$(CF$_2$)$_r$ in which r is 2 to 18; and q is 1, 2 or 3.

In a more particular embodiment, $R^f$ is a mixture of said perfluoroalkyl groups, CF$_3$CF$_2$(CF$_2$)$_r$; and r is 2, 4, 6, 8, 10, 12, 14, 16, and 18. In a preferred embodiment, r is predominantly 4, 6 and 8; e.g. see Example 1. In another preferred embodiment, r is predominantly 6 and 8; e.g. see Example 44. The former preferred embodiment is more readily available commercially and is therefore less expensive, while the latter may provide improved properties.

Representative fluoroaliphatic alcohols that can be used for the purposes of this invention are:

C$_s$F$_{2s+1}$(CH$_2$)$_t$OH (CF$_3$)$_2$CFO(CF$_2$CF$_2$)$_u$CH$_2$CH$_2$OH

C$_s$F$_{2s+1}$CON(R$^8$) (CH$_2$)$_t$OH

C$_s$F$_{2s+1}$SO$_2$N(R$^8$) CH$_2$)$_t$OH

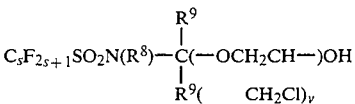

wherein s is 3 to 14;

t is 1 to 12;

u is 1 to 5;

each of R$^8$ & R$^9$ is H or alkyl containing 1 to 6 carbon atoms

In another embodiment, the fluorochemical compound which contains a single functional group can be represented by the formula: H(CF$_2$CF$_2$)$_w$CH$_2$OH wherein w is 1–10. The latter fluorochemical compound is a known fluorochemical compound which can be prepared by reacting tetrafluoroethylene with methanol. Yet another such compound is 1,1,1,2,2,2-hexafluoroisopropanol having the formula: CF$_3$(CF$_3$)CHOH.

In yet another embodiment of the invention, a non-fluorinated organic compound which contains a single functional group can be used in conjunction with one or more of said fluorochemical compounds. Usually between about 1% and about 60% of the isocyanate groups of the polyisocyanate are reacted with at least one such nonfluorinated compound. For example, said non-fluorinated compound can be represented by the formula:

$$R^{10}-R^{11}{}_k-YH$$

wherein

R$^{10}$ is a C$_1$–C$_{18}$ alkyl, a C$_1$–C$_{18}$ omega-alkenyl radical or a C$_1$–C$_{18}$ omega-alkenoyl;

R$^{11}$ is

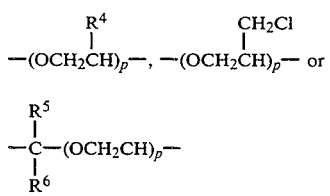

in which R$^4$, R$^5$ and R$^6$ are the same or different H or alkyl radical containing 1 to 6 carbon atoms and p is 1 to 50;

Y is —O—, —S—, or —NR$^7$)— in which R$^7$ is H or alkyl containing 1 to 6 carbon atoms; and k and p are as defined above.

For example, the nonfluorinated compound can be an alkanol or a monoalkyl or monoalkenyl ether or ester of a polyoxyalkylene glycol. Particular examples of such compounds include stearyl alcohol, the monomethyl ether of polyoxethylene glycol, the mono-allyl or -methallyl ether of polyoxethylene glycol, the monomethacrylic or acrylic acid ester of polyoxethylene glycol, and the like.

Any polyisocyanate having three or more isocyanate groups can be used for the purposes of this invention. For example, one can use hexamethylene diisocyanate homopolymers having the formula:

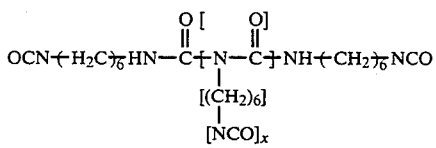

wherein x is an integer equal to or greater than 1, preferably between 1 and 8. Because of their commercial availability, mixtures of such hexamethylene diisocyanate homopolymers are preferred for purposes of this invention. Also of interest are hydrocarbon diisocyanate-derived isocyanurate trimers which can be represented by the formula:

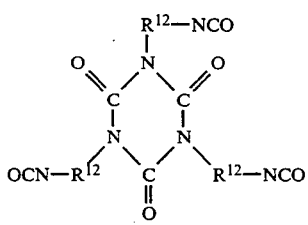

wherein $R^{12}$ is a divalent hydrocarbon group, preferably aliphatic, alicyclic, aromatic or arylaliphatic. For example, $R^{12}$ can be hexamethylene, toluene or cyclohexylene, preferably the former. Other polyisocyanates useful for the purposes of this invention are those obtained by reacting three mols of toluene diisocyanate with 1,1,1-tris-(hydroxymethyl)-ethane or 1,1,1-tris-(hydroxymethyl)-propane. The isocyanurate trimer of toluene diisocyanate and that of 3-isocyanatomethyl-3,4,4-trimethylcyclohexyl isocyanate are other examples of polyisocyanates useful for the purposes of this invention, as is methine-tris-(phenylisocyanate). Also useful for the purposes of this invention is the polyisocyanate having the formula:

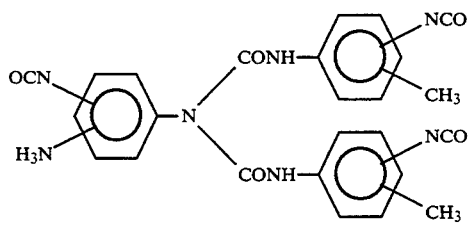

The polyfluoro organic compounds of the invention are prepared by reacting: (1) at least one polyisocyanate or mixture of polyisocyanates which contains at least three isocyanate groups per molecule with (2) at least one fluorochemical compound which contains per molecule (a) a single functional group having one or more Zerewitinoff hydrogen atoms and (b) at least two carbon atoms each of which contains at least two fluorine atoms. Thereafter the remaining isocyanate groups are reacted with water to form one or more urea linkages. Usually between about 40% and about 95% of the isocyanate groups will have been reacted before water is reacted with the polyisocyanate. In other words, the amount of water generally is sufficient to react with from about 5% to about 60% of the isocyanate groups in the polyisocyanate. Preferably, between about 60% and 90% of the isocyanate groups have been reacted before water is reacted with the polyisocyanate, and most preferably between about 70% and 85% of the isocyanate groups have been reacted prior to reaction of water with the polyisocyanate. Thus, in a preferred embodiment the amount of water is sufficient to react with about 10% to about 35% of the isocyanate groups, most preferably between 15% and 30%.

In one embodiment, water-modified fluorochemical carbamates have been prepared by the sequential catalyzed reaction of Desmodur N-100, Desmodur N-3200 or Desmodur N-3300, or mixtures thereof, with a stoichiometric deficiency of a perfluoroalkyl compound containing one functional group, and then with water. Desmodur N-100 and Desmodur N-3200 are hexamethylene diisocyanate homopolymers commercially available from Mobay Corporation. Both presumably are prepared by the process described in U.S. Pat. No. 3,124,605 and presumably to give mixtures of the mono, bis, tris, tetra and higher order derivatives which can be represented by the general formula:

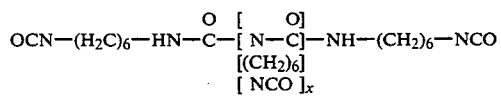

wherein x is an integer equal to or greater than 1, preferably between 1 and 8.

| Typical Properties | Ave. Ea. Wt. | NCO Content, % |
|---|---|---|
| Desmodur N-100 | 191 | 22.0 |
| Desmodur N-3200 | 181 | 23.2 |

The typical NCO content of Desmodur N-100 approximates that listed for a SRI International Report (Isocyanates No. 1D, July, 1983, Page 279) hexamethylene diisocyanate homopolymer with the following composition:

| Product Composition | Wt. % |
|---|---|
| Hexamethylene diisocyanate | 0.1 |
| Monobioret | 44.5 |
| Bisbiuret | 17.4 |
| Trisbiuret | 9.5 |
| Tetrabiuret | 5.4 |
| Higher Mol. Wt. Derivatives | 23.1 |
| NCO Content | 21.8 |

Based on its average equivalent weight and NCO content, the comparative bis, tris, tetra, etc., content of Desmodur N-3200 should be less than that of the N-100 product. Desmodur N-3300 is a hexamethylene diisocyanate-derived isocyanurate trimer which can be represented by the formula:

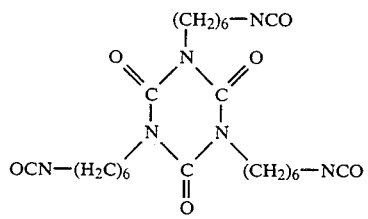

The water-modified fluorochemical carbamates are typically prepared by first charging the polyisocyanate, the perfluoroalkyl compound and a dry organic solvent such as methyl isobutyl ketone (MIBK) to a reaction vessel. The order of reagent addition is not critical. The specific weight of aliphatic polyisocyanate and perfluoroalkyl compounds charged is based on their equivalent weights and on the working capacity of the reaction vessel and is adjusted so that all Zerewitinoff active hydrogens charged will react with some desired value between 40% and 95% of the total NCO group charge. The weight of dry solvent is typically 15%-30% of the total charge weight. The charge is agitated under nitrogen and heated to 40°-70° C. A catalyst, typically dibutyltindilaurate per se, or as a solution in methylisobutylketone (MIBK), is added in an amount which depends on the charge, but is usually small, e.g. 1 to 2 parts per 10,000 parts of the polyisocyanate. After the resultant exotherm, the mixture is agitated at a temperature between 65° and 105° C. for 2-20 hours from the time of the catalyst addition, and then, after its temperature is adjusted to between 55° and 90° C., is treated with water per se or with wet MIBK for an additional 1 to 20 hours. The resultant product can be stored and/or used as prepared or after further solvent dilution or converted by standard technology to an aqueous emulsion or dispersion. In some instances, the emulsion or dispersion is surfactant-stabilized; in others, a stable emulsion or dispersion can be prepared without the use of a surfactant, e.g. that of Example 53.

Suitable substrates for the application of the products of this invention are films, fibers, yarns, fabrics, carpeting, and other articles made from filaments, fibers, or yarns derived from natural, modified natural, or synthetic polymeric materials or from blends of these other fibrous materials and other porous materials which will absorb and transport low surface tension liquids either on their surfaces on in their interstices by capillary action. Specific representative examples are cotton, silk, regenerated cellulose, nylon, fiber-forming linear polyesters, fiber-forming polyacrylonitrile, cellulose nitrate, cellulose acetate, ethyl cellulose, paper, fiberglass, wood pressed or otherwise hardened wood composites, metals, unglazed porcelain, porous concrete and the like. Dyed and undyed cotton sateen, poplin, broadcloth, jean cloth, gabardine and the like are especially adaptable for treatment with the compositions of this invention to provide products having a high repellency to oil and water and which are also relatively unaffected by the action of heat, air and light. Materials rendered oil and water-repellent by the products of this invention retain a high portion of the original repellency after laundering and dry cleaning. The novel compounds of this invention impart oil-, water- and soil-repellency and/or soil-release properties to fibrous and non-fibrous substrates.

Two types of substrates are of particular interest in accordance with the present invention. One of those is carpeting, particularly nylon carpeting, to which novel compounds of the present invention are applied so as to impart oil-, water- and soil-repellency. The other class of substrates to which it is particularly advantageous to apply the compounds of the present invention so as to impart soil-release properties includes those prepared from polyamide fibers (such as nylon), cotton and blends of polyester and cotton, particularly such substrates being used in tablecloths, washable uniforms and the like. Of particular interest are polyamide carpeting, e.g. nylon carpeting, to which a preferred embodiment illustrated by Example 26 is applied so as to impart oil-, water-, and soil-repellency. In another preferred embodiment, the novel compound exemplified by Example 53 is applied to textile fabrics so as to impart soil-release properties.

The compounds of the present invention can be applied to suitable substrates by a variety of customary procedures. For the carpeting end-use, one can apply them by use of spray or foam applicators, nip rolls, the conventional beck dying procedure, continuous dying procedure or thread-line application. For application to washable apparel fabrics, the compounds of spray or foam applicators, nip rolls, the present invention can be applied, for example, from an aqueous dispersion or an organic solvent solution by brushing, dipping, spraying, padding, roll-coating, foaming or the like. The compounds of this invention can be applied to the substrate as such or in combination with other textile or fluorofinishes, processing aids, lubricants, anti-stains, etc. The compounds can also be blended with other agents which have oil/water repellency and soil release properties and applied to fibers or fabrics. They can be applied to dyed and undyed carpeting and other textile substrates.

The use of a stoichiometric excess of a polyisocyanate assures complete reaction of the fluorinated and non-fluorinated organic compounds; that coupled with subsequent reaction with water provides products of this invention which possess enhanced properties when compared to those of the prior art, particularly when used to treat carpeting, as well as washable fabrics such as table clothes, uniforms and the like. In addition those aspects of the invention eliminate any need to remove any unreacted organic compound. It thus provides a substantial process advantage; it also provides greater product purity and uniformity.

In the Examples that follow, the tests described below were used.

Test No. 1—Wash Stability

Nylon 66 knit fabric is padded with a FREON-113/acetone (1/6 parts by weight) solution of the fluorochemical so as to obtain a uniform coverage of about 700 ppm fluorine (on the weight of the fiber). The air dried fabric sample is annealed for two minutes in a circulating air oven at 394° F., a swatch then taken for fluorine analysis and the remainder subjected to five standard home washing cycles and reanalyzed for flourine content and, for some samples, oil/water repellency. The home washes are carried out in a "Kenmore" washing machine at 40° C., employing 28 grams of "Tide" detergent per washload, followed by drying for 40 minutes in an automatic dryer at medium setting.

Test No. 2—Oil/Water Repellency

Beginning with the lowest numbered test liquid (Repellency Rating No. 1), one drop (approximately 5 mm diameter or 0.05 ml volume) is placed on each of three locations at least 5 mm apart. The drops are observed for 10 seconds for the water-repellency test, 30 seconds for the oil-repellency test. If, at the end of those periods of time, two of the three drops are still spherical to hemispherical in shape with no wicking around the drops, three drops of the next higher numbered test liquid are placed on adjacent sites and observed again for the specified periods of time. The procedure is continued until one of the test liquids results in two of the three drops failing to remain spherical or hemispherical, or wetting or wicking occurs. The oil-repellency rating and the water-repellency rating of the yarn, fabric or carpet each is the highest numbered test liquid for which two of three drops remain spherical or hemispherical with no wicking for the specified time.

STANDARD WATER TEST LIQUIDS

| Water-Repellency Rating Number | Composition (Volume %) | |
|---|---|---|
| | Isopropanol (Reagent Grade) | Distilled $H_2O$ |
| 1 | 2 | 98 |
| 2 | 5 | 95 |
| 3 | 10 | 90 |
| 4 | 20 | 80 |
| 5 | 30 | 70 |

Unless otherwise indicated in the Examples that follow, the fluorinated reactant is the above-described perfluoroalkylethyl alcohol mixture (FA) of the formula: $F(CF_2)_y CH_2CH_2OH$ and/or perfluoroalkylpropyl amine mixture of the formula: $F(CF_2)_y CH_2CH_2CH_2NH_2$, wherein y in each formula is predominantly 6, 8 and 10. In a typical mixture of such fluoroalcohols or amines, the compounds will have the following approximate composition in relation to their $F(CF_2)_y$ radicals:

0% to 3% wherein y=4,
27% to 37% wherein y=6,
28% to 32% wherein y=8,
14% to 20% wherein y=10,
8% to 13% wherein y=12,
3% to 6% wherein y=14,
0% to 2% wherein y=16,
0% to 1% wherein y=18, and
0% to 1% wherein y=20.

Oil and water repellencies are given in Tables 1 and 2 under the heading "O/W". In some of the Examples, the above-described two-step procedure was used in which a polyisocyanate containing at least three NCO groups was reacted with a perfluoroalkyl alcohol and/or amine to obtain an intermediate product in which the perfluoroalkyl and isocyanate group-containing moieties are linked by a urethane or urea group, respectively. In other Examples, a non-fluorinated organic compound which contains a single functional group was reacted with the polyisocyanate along with the fluoroalcohol and/or fluoroamine. The subsequent reaction of water with the residual NCO groups is presumed to predominantly yield urea group linked products by one or both of the following reaction pathways:

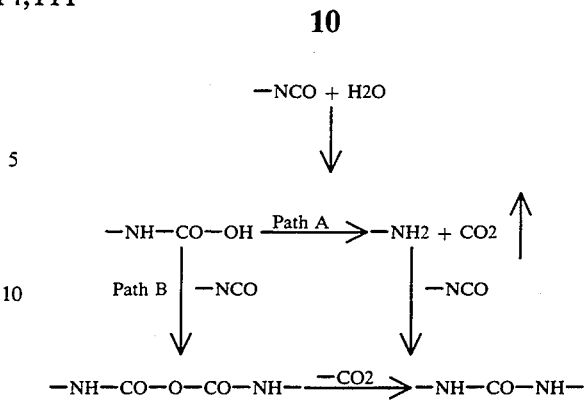

Water reacting by either of the two pathways acts as a dual functional Zerewitinoff active hydrogen compound. It is convenient to describe the amount of water added to a synthesis mixture in terms of the amount of Zerewitinoff active hydrogens added per number of residual NCO groups, ie as a ratio. The theoretical water ratio required to satisfy the stoichiometry of the two pathways is 1.0.

EXAMPLE 1

A hexamethylene diisocyanate homopolymer (Desmodur N-100) containing 22.05% NCO groups by di-n-butylamine titration method analysis, a perfluoroalkylethyl alcohol mixture (FA) in an amount sufficient to react with 95.1% of the NCO group charge, and dry MIBK in an amount equal to 24.1% of the total charge weight were added to a reaction vessel, agitated under nitrogen and heated to 70° C., whereupon a catalytic amount of dibutyltindilaurate was added. After the resultant exotherm, the reaction mixture was agitated at about 80° C. for 2 hours from the time of the catalyst addition, and then treated with wet MIBK in an amount equal to a water ratio of 8.96. The diluted mixture was agitated at about 65° C. for an additional 2.5 hours. When tested for oil- and water- repellency (O/W) pursuant to Tests 1 and 2, the product gave ratings of 7/6.

EXAMPLES 2-5

The procedure of Example 1 was repeated with the modifications set forth in Table 1.

TABLE 1

| | Step One | | | Step Two | | | |
|---|---|---|---|---|---|---|---|
| Ex. | Rx %* | MIBK % | Cat °C. | Water Ratio | Time, Hours | % F Retained | O/W |
| 2 | 89.3 | 24.9 | 65 | 3.84 | 16 | 64 | 6/6 |
| 3 | 85.0 | 23.5 | 70 | 2.74 | 2.5 | 67 | 7/7 |
| 4 | 79.2 | 24.3 | 60 | 1.85 | 16 | 73 | 7/6 |
| 5 | 69.3 | 24.6 | 62 | 1.13 | 16 | 77 | 6/7 |

*Percentage of available —NCO groups reacted with FA.

EXAMPLE 6

A hexamethylene diisocyanate homopolymer (Desmodur N-3200) containing 22.60% NCO groups by di-N-butylamine titration method analysis, a perfluoroalkylethyl alcohol mixture (FA) in an amount sufficient to react with 59.9% of the NCO group charge, and dry MIBK in an amount equal to 22.4% of the total charge weight were added to a reaction vessel, agitated under nitrogen and heated to 69° C., whereupon a catalytic amount of dibutyltindilaurate was added. After the resultant exotherm, the reaction mixture was agitated at about 80° C. for 2 hours from the time of the catalyst addition, then cooled to 65° C. and treated with wet MIBK in an amount equal to a water ratio of 1.00. The diluted reaction mixture was agitated at about 65° C. for an additional 17.5 hours. The product had an O/W rating of 6/6.

EXAMPLES 7–10

The procedure of Example 6 was repeated with the modifications set forth in Table 2.

TABLE 2

| | Step One | | | Step Two | | | |
|---|---|---|---|---|---|---|---|
| Ex. | Rx %* | MIBK % | Cat °C. | Water Ratio | Time, Hours | % F Retained | O/W |
| 7 | 66.5 | 22.6 | 63 | 1.00 | 17 | 81 | 7/7 |
| 8 | 73.7 | 22.9 | 65 | 1.00 | 17 | 70 | 7/7 |
| 9 | 80.0 | 23.0 | 68 | 1.00 | 18 | 71 | 7/7 |
| 10 | 89.6 | 23.2 | 67 | 1.01 | 18 | 64 | 7/6 |

EXAMPLE 11

A hexamethylene derived isocyanurate trimer (Desmodur N-3300) containing 21.65% NCO groups by di-N-butylamine titration method analysis, a perfluoroalkylethyl alcohol mixture (FA) in an amount sufficient to react with 59.9% of the NCO group charge and dry MIBK in an amount equal to 22.1% of the total charge weight were added to a reaction vessel, agitated under nitrogen and heated to 59° C., whereupon a catalytic amount of dibutyltindilaurate was added. After the resultant exotherm, the reaction mixture was agitated at about 80° C. for 4.25 hours from the time of the catalyst addition, and then treated with wet MIBK in an amount equal to a water ratio of 1.58. The diluted mixture was agitated at about 65° C. for an additional 17 hours.

EXAMPLES 12–14

The procedure of Example 6 was repeated with the modifications set forth in Table 3.

TABLE 3

| | Step One | | | Step Two | |
|---|---|---|---|---|---|
| Ex. | Rx % | MIBK % | Cat °C. | Water Ratio | Time Hours |
| 12 | 70.0 | 22.0 | 62 | 2.46 | 17 |
| 13 | 79.9 | 22.3 | 60 | 2.04 | 17 |
| 14 | 89.2 | 22.7 | 62 | 4.08 | 17 |

EXAMPLE 15

A hexamethylene diisocyanate homopolymer (Desmodur N-3200) and a hexamethylene derived isocyanurate (Desmodur N-3300) containing respectively 22.51% and 21.65% NCO groups by di-N-butylamine titration method analysis, were charged to a reaction vessel in relative amounts that the biuret mixture contributed 74.9% of the total NCO group charge, along with a perfluroalkylethyl alcohol (FA) in an amount sufficient to react with 69.9% of the total NCO group charge, and dry MIBK in an amount equal to 22.2% of the total charge weight. The mixture was agitated under nitrogen and heated to 69° C., whereupon a catalytic amount of dibutyltindilaurate was added. After the resultant exotherm, the reaction mixture was agitated at about 80° C. for 2 hours from the time of the catalyst addition and then treated with wet MIBK in an amount equal to a water ratio of 2.44. The diluted reaction mixture was agitated at about 65° C. for 4 additional hours.

EXAMPLE 16

The procedure of Example 15 was repeated except the biuret mixture contributed 87.6% of the total NCO group charge.

EXAMPLE 17

A hexamethylene diisocyanate homopolymer (Desmodur N-3200) containing 22.54% NCO groups by di-N-butylamine titration method analysis, a perfluoroalkylethyl alcohol mixture (FA) in an amount sufficient to react with 59.9% of the total NCO group charge, a perfluoroalkylpropyl amine mixture in an amount sufficient to react with 10.0% of the total NCO group charge and dry MIBK in an amount equal to 21.9% of the total charge weight were added to a reaction vessel, agitated under nitrogen and heated to 57° C., whereupon a catalytic amount of dibutyltindilaurate was added. After the resultant exotherm, the reaction mixture was agitated at about 80° C. for 3.25 hours from the time of the catalyst addition, and then treated with wet MIBK in an amount equal to a water ratio of 1.25. The diluted reaction mixture was agitated at about 65° C. for an additional 17.5 hours.

EXAMPLE 18

The product was prepared by the procedure of Example 17 except the perfluoroalkylethyl alcohol mixture (FA) and the perfluoroalkylpropyl amine mixture were added in amounts sufficient to react with 50.0% and 20.0%, respectively, of the total NCO group charge.

EXAMPLE 19

A hexamethylene diisocyanate homopolymer (Desmodur N-3200) containing 22.66% NCO groups by di-N-butylamine titration method analysis, a perfluoroalkylethyl alcohol mixture (FA) in an amount sufficient to react with 70.1% of the NCO group charge, and dry MIBK in an amount equal to 22.9% of the total charge weight were added to a reaction vessel, agitated under nitrogen and heated to 60° C., whereupon a catalytic amount of dibutyltindilaurate was added. After the resultant exotherm, the reaction mixture was agitated at about 80° C. for three hours from the time of the catalyst addition, then cooled to 61° C. and treated with water in an amount equal to a water ratio of 38.62. The treated mixture was agitated at about 65° C. for an additional 17 hours.

EXAMPLE 20

The product was prepared from a hexamethylene diisocyanate homopolymer (Desmodur N-3200) containing 22.60% NCO groups by di-N-butylamine titration method analysis by the procedure of Example 19, with MIBK at 22.8%, a temperature of 57° C. at the time that the catalyst was added, a water ratio of 1.00, and a reaction period of 18 hours in the second step.

EXAMPLE 21

A hexamethylene diisocyanate homopolymer (Desmodur N-3200) containing 22.53% NCO groups by di-N-butylamine titration method analysis, a perfluoroalkylethyl alcohol mixture (FA) in an amount sufficient to react with 69.9% of the NCO group charge, and dry MIBK in an amount equal to 22.2% of the total charge weight were added to a reaction vessel, agitated under nitrogen and heated to 65° C., whereupon a catalytic amount of dibutyltindilaurate was added. After the resultant exotherm, the reaction mixture was agitated at about 80° C. for two hours from the time of the catalyst addition, and then treated with three approximately equal portions of water at 178 hour intervals in a total amount corresponding to a water ratio of 1.43. The treated mixture was agitated at about 80° C. for four hours from the first addition of water.

EXAMPLE 22

A hexamethylene diisocyanate homopolymer (Desmodur N-3200) in dry methylisobutylketone solution containing 13.69% NCO groups by di-N-butylamine titration method analysis and a perfluoroalkylethyl alcohol mixture (FA) in an amount sufficient to react with 50.0% of the NCO group charge were added to a reaction vessel, agitated under nitrogen and heated to 62° C. whereupon a catalytic amount of dibutyltindilaurate was added. After the resultant exotherm, the reaction mixture was agitated at about 80° C. for two hours from the time of the catalyst addition, and then treated with wet MIBK in an amount equal to a water ratio of 0.99. The diluted mixture was agitated at about 65° C. for an additional 18 hours. The product gave an O/W rating of 5/8.

EXAMPLES 23-27

The procedure of Example 22 was repeated with the modifications set forth in Table 4.

TABLE 4

| Ex. No. | Step One | | Step Two | | |
|---|---|---|---|---|---|
| | Rx, % | Cat., °C. | Water Ratio | Ratio Hours | O/W |
| 23 | 54.7 | 62 | 1.16 | 17 | 5/7 |
| 24 | 60.0 | 62 | 1.43 | 17 | 5/7 |
| 25 | 70.0 | 62 | 2.21 | 16 | 6/8 |
| 26 | 75.0 | 62 | 2.83 | 16 | 6/8 |
| 27 | 90.0 | 60 | 1.11 | 17 | 5/5 |

EXAMPLE 28

A hexamethylene diisocyanate homopolymer (Desmodur N-3200) in dry methylisobutylketone solution containing 13.69% NCO groups by di-N-butylamine titration method analysis, a perfluoroalkylethyl alcohol mixture (FA) in an amount sufficient to react with 70.0% of the NCO group charge and 1-octadecanol (stearyl alcohol) in an amount sufficient to react with 20.0% of the NCO group charge were added to a reaction vessel, agitated under nitrogen and heated to 62° C., whereupon a catalytic amount of dibutyltindilaurate was added. After the resultant exotherm, the reaction mixture was agitated at about 80° C. for 2 hours from the time of the catalyst addition and then treated with wet MIBK in an amount equal to a water ratio of 7.41. The diluted reaction mixture was agitated at about 65° C. for an additional 17 hours.

EXAMPLE 29

A hexamethylene diisocyanate homopolymer (Desmodur N-3200) in dry MIBK solution containing 13.66% NCO groups by di-N-butylamine titration method analysis, a perfluoroalkylethyl alcohol mixture (FA) in an amount sufficient to react with 75.0% of the NCO group charge and a monomethyl ether of a poly(oxyethylene) glycol, 750 average molecular weight (MPEG 750), in an amount sufficient to react with 20.0% of the NCO group charge were added to a reaction vessel, agitated under nitrogen and heated to 62° C., whereupon a catalytic amount of dibutyltindilaurate was added. After the resultant exotherm, the reaction mixture was agitated at about 80° C. for 2 hours from the time of the catalyst addition and then treated with wet MIBK in an amount equal to a water ratio of 21.09. The diluted reaction mixture was agitated at about 65° C. for an additional 2 hours.

EXAMPLE 30

The procedure of Example 29 was repeated except that the amount of MPEG 750 was sufficient to react with 10% of the NCO group charge, and the water ratio was 6.02.

EXAMPLE 31

The procedure of Example 29 was repeated except that the amount of MPEG 750 was sufficient to react with 5.0% of the NCO group charge, and the water ratio was 4.11.

EXAMPLE 32

The procedure of Example 29 was repeated except that the amount of FA was sufficient to react with 73.0% of the NCO group charge; the amount of MPEG 750 was sufficient to react with 2.0% of the NCO group charge, and the water ratio was 3.05.

EXAMPLE 33

A hexamethylene (Desmodur N-3200) in dry MIBK solution containing 13.52% NCO groups by di-N-butylamine titration method analysis and a perfluoroalkylethyl alcohol mixture (FA) in an amount sufficient to react with 40.0% of the NCO group charge were added to a reaction vessel, agitated under nitrogen and heated to 60° C., whereupon a catalytic amount of dibutyltindilaurate was added. After the resultant exotherm, the reaction mixture was agitated at about 80° C. for two hours from the time of the catalyst addition and then treated with wet MIBK in an amount equal to a water ratio of 1.05:1. The diluted reaction mixture was agitated at about 65° C. for an additional two hours.

EXAMPLE 34

Example 33 was repeated except that the amount of FA was sufficient to react with 45.0% of the NCO group charge; the temperature was 62° C., and the water ratio was 1.07.

EXAMPLE 35

A hexamethylene diisocyanate homopolymer (Desmodur N-3200) in dry MIBK solution containing 13.66% NCO groups by di-N-butylamine titration method analysis and a perfluoroalkylethyl alcohol mixture (FA) in an amount sufficient to react with 95.0% of the NCO group charge were added to a reaction vessel, agitated under nitrogen and heated to 60° C. whereupon a catalytic amount of dibutyltindilaurate was added. After the resultant exotherm, the reaction mixture was agitated at about 80° C. for two hours from the time of the catalyst addition, and then treated with wet MIBK in an amount equal to a water ratio of 18.78. The diluted reaction mixture was agitated at about 85° C. for an additional two hours.

EXAMPLE 36

A mixture of hexamethylene diisocyanate homopolymer (Desmodur N-3200) in dry MIBK (containing 13.52% NCO groups by di-N-butylamine titration method analysis) and 2,2,2,3,3,3-hexafluoroisopropanol in an amount sufficient to react with 80.0% of the NCO group charge were added to a reaction vessel and agitated under nitrogen. After the resultant exotherm, the reaction mixture was heated to 63° C., whereupon a catalytic amount of dibutyltindilaurate was added. The reaction mixture was heated further to and held at about 80° C. for two hours from the time of the catalyst addition, and then treated with wet MIBK in an amount equal to a water ratio of 1.58. The diluted reaction mixture was agitated at about 65° C. for an additional two hours.

EXAMPLE 37

A hexamethylene diisocyanate homopolymer (Desmodur N-3200) in dry MIBK solution containing 13.52% NCO groups by di-N-butylamine titration method analysis and 2,2,3,3-tetrafluoro-1-propanol in an amount sufficient to react with 75.0% of the NCO group charge were added to a reaction vessel, agitated under nitrogen and heated to 60° C., whereupon a catalytic amount of dibutyltindilaurate was added. After the resultant exotherm, the reaction mixture was agitated at about 80° C. for two hours from the time of the catalyst addition, and then treated with wet MIBK in an amount equal to a water ratio of 1:1. The diluted reaction mixture was agitated at about 65° C. for an additional two hours.

EXAMPLE 38

A hexamethylene diisocyanate homopolymer (Desmodur N-3200) containing 22.54% NCO groups by di-N-butylamine titration method analysis, N-methyl-N-ethanolperfluorooctane sulfonamide in an amount sufficient to react with 70.0% of the total NCO group charge, and dry MIBK in an amount equal to 22.3% of the total charge weight were added to a reaction vessel, agitated under nitrogen and heated to 60° C. for three hours from the time of the catalyst addition, and then treated with wet MIBK in an amount equal to a water ratio of 1.36. The diluted mixture was agitated at about 65° C. for an additional 17.5 hours.

EXAMPLE 39

A hexamethylene diisocyanate homopolymer (Desmodur N-3200) containing 22.54% NCO groups by di-N-butylamine titration method analysis, N,N-bis-(perfluorooctylethyl)-amine in an amount sufficient to react with 69.9% of the total NCO group charge, and dry MIBK in an amount equal to 22.5% of the total charge weight were added to a reaction vessel, agitated under nitrogen and heated to 72° C., whereupon a catalytic amount of dibutyltindilaurate was added. The reaction mixture was heated to, and agitated at about 80° C. for about 21 hours from the time the reaction mixture components were charged to the reaction vessel, and then diluted with MIBK in an amount equal to 49.0% of the initial charge weight and treated with water in an amount equal to a water ratio of 1.16. The treated mixture was agitated at about 67° C. for an additional six hours.

EXAMPLE 40

A hexamethylene diisocyanate homopolymer (Desmodur N-3200) containing 22.70% NCO groups by di-N-butylamine titration method analysis, N-propyl-3,4,4,5,5,6,6,7,7,8,8,9,9,10,10,10-hexadecafluoro-2-decene-1-amine (containing about 1.4% N-perfluorooctylethyl-N-propylamine) in an amount sufficient to react with 69.7% of the total NCO group charge and dry MIBK in an amount equal to 17.5% of the total charge weight were added to a reaction vessel and agitated under nitrogen. After the resultant exotherm, the reaction mixture temperature was adjusted to about 80° C. and the mixture was agitated for about 2 hours from the time the reaction mixture components were charged to the reaction vessel. Wet MIBK in an amount equal to a water ratio of 1.38 was then added and the mixture agitated at about 65° C. for an additional 3.25 hours.

EXAMPLE 41

A hexamethylene diisocyanate homopolymer (Desmodur N-3200) containing 22.70% NCO groups by di-N-butylamine titration method analysis, N-propyl-3,4,4,5,5,6,6,7,7,8,8,9,9,10,10,10-hexadecafluoro -2-decen-1-amine (containing about 1.4% N-perfluorooctylethyl-N-propylamine) in an amount sufficient to react with 79.1% of the total NCO group charge, and dry MIBK in an amount equal to 21.0% of the total charge weight were added to a reaction vessel and agitated under nitrogen. After the resultant exotherm, the reaction mixture temperature was adjusted to about 80° C. and the mixture was agitated for two hours from the time the reaction mixture components were charged to the reaction vessel. Wet MIBK in an amount equal to a water ratio of 2.00 was then added and the mixture agitated at about 65° C. for an additional 3.5 hours.

EXAMPLE 42

A hexamethylene diisocyanate homopolymer (Desmodur N-3200) in dry MIBK solution containing 13.66% NCO groups by di-N-butyl amine titration method analysis, a perfluoroalkylethyl alcohol mixture (FA) in an amount sufficient to react with 47.6% of the NCO group charge and a monoallyl ether of a poly(oxyethylene) glycol, 550 average molecular weight, in an amount sufficient to react with 40.0% of the NCO group charge were added to a reaction vessel, agitated under nitrogen and heated to 65° C., whereupon a catalytic amount of dibutyltindilaurate was added. After the resultant exotherm, the reaction mixture was agitated at about 80° C. for two hours from the time of the catalyst addition and then treated with wet MIBK in an amount equal to a water ratio of 7.47. The diluted reaction mixture was agitated at about 65° C. for an additional 22 hours.

EXAMPLE 43

A hexamethylene diisocyanate homopolymer (Desmodur N-3200) in dry MIBK solution containing 13.86% NCO groups by di-N-butyl amine titration method analysis, a perfluoroalkylethyl alcohol mixture (FA) in an amount sufficient to react with 43.6% of the NCO group charge and a monomethyl ether of a poly-(oxyethylene) glycol, 750 average molecular weight (MPEG 750), in an amount sufficient to react with 42.8% of the NCO group charge were added to a reaction vessel, agitated under nitrogen and heated to 63°

C., whereupon a catalytic amount of dibutyltindilaurate was added. After the resultant exotherm, the reaction mixture was agitated at about 90° C. for two hours from the time of the catalyst addition and then treated with wet MIBK in an amount equal to a water ratio of 9.03. The diluted reaction mixture was agitated at about 65° C. for an additional two hours.

EXAMPLE 44

A hexamethylene diisocyanate homopolymer (Desmodur N-3200) in dry MIBK solution containing 13.82% NCO groups by di-N-butyl amine titration method analysis and a perfluoroalkylethyl alcohol mixture (FNA)* in an amount sufficient to react with 74.3% of the NCO group charge were added to a reaction vessel, agitated under nitrogen and heated to 61° C., whereupon a catalytic amount of dibutyltindilaurate was added. After the resultant exotherm, the reaction mixture was agitated at about 80° C. for two hours from the time of the catalyst addition and then treated with wet MIBK in an amount equal to a water ratio of 1.74. The diluted reaction mixture was agitated at about 65° C. for an additional two hours.

* A perfluoroalkylethyl alcohol mixture of the formula: $F(CF_2)_zCH_2CH_2OH$ wherein z is predominantly 8 and 10; in a typical mixture of which the fluoroalcohols will have the following approximate composition in relation to their $F(CF_2)_z$ radicals:

0% to 3% wherein z=6,
45% to 52% wherein z=8,
26% to 32% wherein z=10,
10% to 14% wherein z=12,
2% to 5% wherein z=14,
0% to 2% wherein z=16,
0% to 1% wherein z=18, and
0% to 1% wherein z=20.

EXAMPLE 45

A hexamethylene diisocyanate homopolymer (Desmodur N-3200) in dry MIBK solution containing 13.86% NCO groups by di-N-butyl amine titration method analysis, a perfluoroalkylethyl alcohol mixture (FNA) in an amount sufficient to react with 75.0% of the NCO group charge and a monomethyl ether of a poly(oxyethylene) glycol, 350 average molecular weight, in an amount sufficient to react with 20.0% of the NCO group charge were added to a reaction vessel, agitated under nitrogen, and heated to 65° C., whereupon a catalytic amount of dibutyltindilaurate was added. After the resultant exotherm, the reaction mixture was agitated at about 80° C. for two hours from the time of the catalyst addition and then treated with wet MIBK in an amount equal to a water ratio of 20.91. The diluted reaction mixture was agitated at about 65° C. for an additional two hours.

EXAMPLE 46

A dry MIBK solution of meta-tetramethylxylene diisocyanate (33.88%NCO groups by di-N-butyl amine titration method analysis) and 1,1,1-tris-(hydroxymethyl)ethane in a 3/1 mole ratio was agitated under nitrogen and heated to 70° C., whereupon a catalytic amount of dibutyltindilaurate was added. After the resultant exotherm, the reaction mixture was agitated at about 80° C. for 1.5 hours from the time of the catalyst addition and then cooled over 1.5 hours to 49° C., whereupon a perfluoroalkylethyl alcohol mixture (FA) in an amount sufficient to react with 70.0% of the residual NCO group charge was added. An additional catalytic amount of dibutyltindilaurate was added and the resultant mixture agitated at about 80° C. for three hours from the time of the fluoroalcohol mixture addition, and then treated with wet MIBK in an amount equal to a water ratio of 1.62. The diluted reaction mixture was agitated at about 65° C. for an additional 16 hours.

EXAMPLE 47

A trifunctional polyisocyanate (Mondur CB-75) derived from toluene diisocyanate and 1,1,1-tris(hydroxymethyl)propane containing 12.56% NCO groups by di-N-butyl amine titration method analysis, a perfluoroalkylethyl alcohol mixture (FA) in an amount sufficient to react with 59.6% of the NCO group charge and dry MIBK in an amount equal to 10.8% of the total charge weight were added to a reaction vessel, agitated under nitrogen and heated to 68° C., whereupon a catalytic amount of dibutyltindilaurate was added. After the resultant exotherm, the reaction mixture was agitated at about 80° C. for two hours from the time of the catalyst addition, and then treated with wet MIBK in an amount equal to a water ratio of 1.38. The diluted mixture was agitated at about 65° C. for an additional four hours.

EXAMPLE 48 TO 50

The procedure of Example 47 was repeated with the modifications set forth in Table 5.

TABLE 5

| | Step One | Step Two | |
|---------|----------|----------|-----------|
| Example | Rx. % | Cat. °C. | Water Ratio | Time, Hrs |
| 48 | 69.7 | 60 | 1.36 | 4 |
| 49 | 80.2 | 58 | 2.23 | 4.25 |
| 50 | 89.5 | 67 | 4.52 | 4 |

EXAMPLE 51

A hexamethylene diisocyanate homopolymer (Desmodur N-3200) and a trifunctional polyisocyanate (Mondur CB-75) derived from toluene diisocyanate and 1,1,1-tris(hydroxymethyl)propane containing 22.71% and 12.56% NCO groups by di-N-butylamine titration method analysis, respectively, were charged to a reaction vessel in relative amounts that the hexamethylene diisocyanate homopolymer contributed 75.0% of the total NCO group charge, along with a perfluoroalkylethyl alcohol (FA) in an amount sufficient to react with 69.9% of the total NCO group charge, and dry MIBK in amount equal to 21.9% of the total charge weight. The mixture was agitated under nitrogen and heated to 64° C., whereupon a catalytic amount of dibutyltindilaurate was added. After the resultant exotherm, the reaction mixture was agitated at about 80° C. for two hours from the time of the catalyst addition and then treated with wet MIBK in an amount equal to a water ratio of 1.32. The diluted reaction mixture was agitated at about 65° C. for two additional hours.

EXAMPLE 52

The procedure of Example 51 was repeated except that the perfluoroalkylethyl alcohol was charged in an amount sufficient to react with 80.2% of the total NCO group charge.

EXAMPLE 53

A hexamethylene diisocyanate homopolymer (Desmodur N-3200) in dry MIBK solution containing 13.69% NCO groups by di-N-butyl amine titration method analysis, a perfluoroalkylethyl alcohol mixture (FA) in an amount sufficient to react with 40.0% of the NCO group charge and a monomethyl ether of a poly(oxyethylene) glycol, 750 average molecular weight (MPEG 750), in an amount sufficient to react with 40.0% of the NCO group charge were added to a reaction vessel, agitated under nitrogen and heated to 60° C., whereupon a catalytic amount of dibutyltindilaurate was added. After the resultant exotherm, the reaction mixture was agitated at about 90° C. for two hours from the time of the catalyst addition and then treated with wet MIBK in an amount equal to a water ratio of 2.48. The diluted reaction mixture was agitated at about 65° C. for an additional two hours. Then water was added and the mixture was solvent-stripped by reduced pressure azeotropic distillation to obtain a 41.6% solids content aqueous dispersion.

We claim:

1. A polyfluoro organic compound having at least one urea linkage, which compound is the product of the reaction of: (1) at least one organic polyisocyanate containing at least three isocyanate groups, (2) at least one fluorochemical compound which contains per molecule (a) a single functional group having one or more Zerewitinoff hydrogen atoms and (b) at least two carbon atoms each of which contains at least two fluorine atoms, and (3) water in an mount sufficient to react with from about 5% to about 60% of the isocyanate groups in said polyisocyanate.

2. The polyfluoro organic compound of claim 1 wherein the amount of water is sufficient to react with about 10% to about 35% of said isocyanate groups.

3. The polyfluoro organic compound of claim 2 wherein the amount of water is sufficient to react with about 15% to 30% of said isocyanate groups.

4. The polyfluoro organic compound of claim 1 wherein said fluorochemical compound which contains a single functional group is represented by the formula:

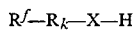

in which $R^f$ is a monovalent aliphatic group containing at least two carbon atoms each of which contains at least two fluorine atoms;

R is a divalent organic radical;

k is 0 or 1; and

X is —O—, —S—, or —N($R^1$)— in which $R^1$ is H, alkyl containing 1 to 6 carbon atoms or a $R^f$—$R_k$— group.

5. The polyfluoro organic compound of claim 4 wherein said fluorochemical compound which contains a single functional group is represented by the formula:

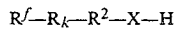

wherein

R is the divalent radical: —$C_mH_{2m}$SO—, —$C_mH_{2m}SO_2$—, —$SO_2N(R^2)$—, or —$CON(R^2)$— in which m is 1 to 22 and $R^2$ is H or alkyl of 1 to 6 carbon atoms;

$R^2$ is the divalent linear hydrocarbon radical: —$C_nH_{2n}$— which can be optionally end-capped by

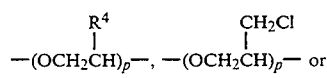

-continued

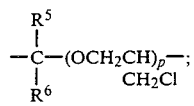

n is 0 to 12, p is 1 to 50, and $R^4$, $R^5$ and $R^6$ are the same or different H or alkyl containing 1 to 6 carbon atoms; and X is —O—, —S—, or —N($R^7$)— in which $R^7$ is H, alkyl containing 1 to 6 carbon atoms or a $R^f$—$R_k$—$R^2$— group.

6. The polyfluoro organic compound of claim 5 wherein $R^f$ is a fully-fluorinated straight or branched aliphatic radical of 3 to 20 carbon atoms which can be interrupted by oxygen atoms.

7. The polyfluoro organic compound of claim 6 wherein said fluorochemical compound which contains a single functional group is represented by the formula:

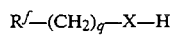

in which $R^f$ is a mixture of perfluoroalkyl groups, $CF_3CF_2(CF_2)_r$ in which r is 2 to 18; and q is 1, 2 or 3.

8. The polyfluoro organic compound of claim 7 wherein $R^f$ is a mixture of said perfluoroalkyl groups, $CF_3CF_2(CF_2)_r$; and r is 2, 4, 6, 8, 10, 12, 14, 16, and 18.

9. The polyfluoro organic compound of claim 8 wherein X is oxygen and q is 2.

10. The polyfluoro organic compound of claim 8 wherein r is predominantly 4, 6 and 8.

11. The polyfluoro organic compound of claim 8 wherein r is predominantly 6 and 8.

12. The polyfluoro organic compound of claim 8 wherein X is —N($R^7$)—, $R^7$ is H and q is 2.

13. The polyfluoro organic compound of claim 4 wherein said fluorochemical compound contains a single functional group is represented by the formula: $H(CF_2CF_2)_wCH_2OH$ in which w is 1–10.

14. The polyfluoro organic compound of claim 4 wherein said fluorochemcial compound which contains a single functional group is represented by the formula: $CF_3(CF_3)CHOH$.

15. The polyfluoro organic compound of claim 1 further characterized in that between about 1% and about 60% of said isocyanate groups are reacted with at least one non-fluorinated organic compound which contains a single functional group.

16. The polyfluoro organic compound of claim 15 wherein said non-fluorinated organic compound is represented by the formula:

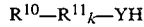

wherein $R^{10}$ is a $C_1$-$C_{18}$ alkyl, a $C_1$-$C_{18}$ omega-alkenyl radical or a $C_1$-$C_{18}$ omega-alkenoyl;

$R^{11}$ is

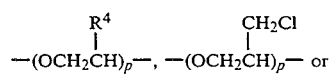

-continued

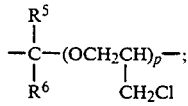

$R^4$, $R^5$ and $R^6$ are the same or different H or alkyl radical containing 1 to 6 carbon atoms and p is 1 to 50;

k is 0 or 1; and

Y is —O—, —S—, or —N($R^7$)— in which $R^7$ is H or alkyl containing 1 to 6 carbon atoms.

17. The polyfluoro organic compound of claim 16 wherein said non-fluorinated compound is an alkanol.

18. The polyfluoro organic compound of claim 16 wherein said non-fluorinated compound is a monoalkyl ether of a poly(oxyalkylene) glycol.

19. The polyfluoro organic compound of claim 8 wherein said non-fluorinated compound is a monomethyl ether of a poly(oxyethylene) glycol.

20. The polyfluoro organic compound of claim 16 wherein said non-fluorinated compound is a monoalkenyl ether of a poly(oxyalkylene) glycol.

21. The polyfluoro organic compound of claim 20 wherein said non-fluorinated compound is a monoallyl ether of a poly(oxyethylene) glycol.

22. A polyfluoro organic compound having at least one urea linkage, which compound is the product of the reaction of: (1) at least one polyisocyanate containing at least three isocyanate groups, (2) at least one fluorochemical compound which contains per molecule (a) a single functional group having one or more Zerewitinoff hydrogen atoms and (b) at least two carbon atoms each of which contains at least two fluorine atoms, and (3) water in an amount sufficient to react with from about 5% to about 60% of the isocyanate groups in said polyisocyanate, wherein said polyisocyanate is represented by the formula:

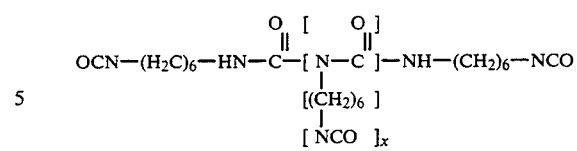

wherein x is an integer equal to or greater than 1.

23. The polyfluoro organic compound of claim 22 wherein x is 1 to 8.

24. A polyfluoro organic compound having at least one urea linkage, which compound is the product of the reaction of: (1) at least one polyisocyanate containing at least three isocyanate groups, (2) at least one fluorochemical compound which contains per molecule (a) a single functional group having one or more Zerewitinoff hydrogen atoms and (b) at least two carbon atoms each of which contains at least two fluorine atoms, and (3) water in an amount sufficient to react with from about 5% to about 60% of the isocyanate groups in said polyisocyanate, wherein said polyisocyanate is represented by the formula:

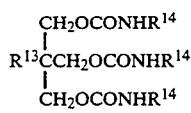

wherein $R^{13}$ is methyl or ethyl, and $R^{14}$ is 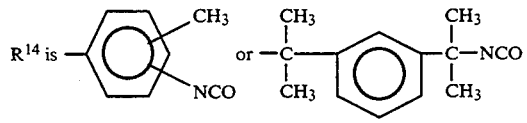

* * * * *